US012648878B2

(12) United States Patent
Owen

(10) Patent No.: US 12,648,878 B2
(45) Date of Patent: Jun. 9, 2026

(54) ENHANCED TRAUMA BANDAGE

(71) Applicant: Jonathan Owen, Brightwood, VA (US)

(72) Inventor: Jonathan Owen, Brightwood, VA (US)

( * ) Notice: Subject to any disclaimer, the term of this patent is extended or adjusted under 35 U.S.C. 154(b) by 461 days.

(21) Appl. No.: 17/428,719

(22) PCT Filed: Apr. 6, 2020

(86) PCT No.: PCT/US2020/026963
§ 371 (c)(1),
(2) Date: Oct. 4, 2023

(87) PCT Pub. No.: WO2020/163880
PCT Pub. Date: Aug. 13, 2020

(65) Prior Publication Data
US 2022/0110798 A1    Apr. 14, 2022

Related U.S. Application Data

(60) Provisional application No. 62/801,899, filed on Feb. 6, 2019.

(51) Int. Cl.
A61F 13/00 (2024.01)
A61F 13/02 (2006.01)
A61F 13/0206 (2024.01)

(52) U.S. Cl.
CPC .... A61F 13/0273 (2013.01); A61F 13/00076 (2013.01); A61F 13/00085 (2013.01); A61F 13/0206 (2013.01); A61F 2013/00119 (2013.01)

(58) Field of Classification Search
CPC .. A61F 2013/00106; A61F 2013/00119; A61F 2013/00288; A61F 2013/00468; A61F 13/00; A61F 13/00038; A61F 15/00; A61F 13/00021; A61F 13/00063; A61B 17/1322
See application file for complete search history.

(56) References Cited

U.S. PATENT DOCUMENTS

| | | | | |
|---|---|---|---|---|
| 6,573,419 | B2 * | 6/2003 | Naimer | A61F 13/0273 602/41 |
| 8,697,931 | B2 * | 4/2014 | Suutari | A61F 15/005 602/53 |
| 9,867,965 | B1 * | 1/2018 | Kantor | A61F 13/12 |
| 11,564,696 | B2 * | 1/2023 | Bagby | A61B 17/1322 |
| 2002/0052570 | A1 | 5/2002 | Naimer | |
| 2003/0199801 | A1 | 10/2003 | Harder | |
| 2007/0185428 | A1 | 8/2007 | Harder | |
| 2007/0260165 | A1 | 11/2007 | Johnson | |
| 2007/0260166 | A1 | 11/2007 | Johnson | |

(Continued)

FOREIGN PATENT DOCUMENTS

CN        200984285        12/2007

*Primary Examiner* — Kim M Lewis
(74) *Attorney, Agent, or Firm* — MEDLER FERRO WOODHOUSE & MILLS PLLC

(57)        ABSTRACT

Disclosed is an enhanced trauma bandage suitable for use as a compression dressing, the structure including an elastic bandage roll, a pass-through structure attached to one end of the elastic bandage roll, a pass-through structure having both an opening and a bandage guide structure at one edge of the opening; a support surface on a lower surface of the pass-through structure; and an absorbent pad removably attached to the lower surface of the pass-through structure.

17 Claims, 11 Drawing Sheets

(56)                    References Cited

U.S. PATENT DOCUMENTS

2011/0319798 A1 *  12/2011  DiGrazia  .............. A61F 15/004
                                                             602/54
2015/0018742 A1     1/2015  Baumgartner
2015/0094756 A1     4/2015  Kosiorek et al.

* cited by examiner

300

ENHANCED TRAUMA BANDAGE

PRIORITY CLAIM

Applicant claims priority from U.S. Provisional Patent Application No. 62/801,899, filed Feb. 6, 2019, in the United States Patent and Trademark Office, the contents of which are hereby incorporated, in its entirety, by reference.

FIELD AND BACKGROUND OF THE INVENTION

The present invention relates to an improved trauma bandage that provides for the rapid and effective dressing of traumatic injuries in the field or hospital setting for controlling bleeding from the wound. More particularly, to a wound dressing and wound dressing system whereby the wound may be rapidly and effectively dressed, easily using only one hand to self-apply if necessary and easily reconfigurable for effective application to a number of different types of wounds.

Bleeding control is a major consideration in the emergency treatment of significant open wounds. Rapid and effective application of compression, at or near the initial injury scene, that can be maintained until the injured person arrives at a medical treatment facility, e.g., a field hospital (FH) or a larger combat support hospital (CSH) where more sophisticated treatment options are available, will reduce blood loss, and improve the patient outcome and survivability of such injuries.

Traditional methods for controlling bleeding and thereby preventing or delaying the onset of hypovolemic shock, include direct compression, applied directly to the wound surface, wound packing in which additional absorbent materials/layers are forced into the wound, focused arterial pressure using a device for providing increased pressure in select areas under the bandage, and/or an extremity tourniquet. Direct compression is often effective in controlling bleeding by achieving high local pressures, which compresses veins and or arteries stopping or restricting blood flow and allowing for clotting, but can be impractical in many emergency situations resulting from the need for continuous application by one or more emergency care providers, thereby limiting the care providers' availability for other tasks. Further, the absorbent dressings may become saturated with blood, the compression may compromise or aggravate damage to other tissues, increase the pain experienced by the injured person, and/or be difficult to apply effectively to some portions of the injured person's body whether by a care provider or oneself.

Extremity tourniquets, consisting of an elastic or non-elastic material bound tightly around a wounded limb and proximal to the wound are effective at producing ischemia in the more distal portions of the wounded limb. While effective at reducing blood loss, the ischemia can be extremely painful for the injured person and will frequently result in soft tissue and/or neurological damage to affected portions of the wounded limb. One technique for preventing or mitigating the undesired effects associated with use of extremity tourniquets involves periodically reducing the pressure applied by the tourniquet and allowing some limited blood flow into the ischemic portion of the wounded limb, thereby increasing blood loss and requiring the services of one or more emergency care providers. Tourniquets are also not suitable for reducing blood loss across a broader range of injuries to locations beyond limbs. Such areas where tourniquets are ineffective include the junctional areas of the shoulders and pelvic region as well as the neck, head, and torso.

Elastic compression bandages, applied directly over the wound surface, are capable of providing significant compression and may be used for securing wound dressings. Elastic bandages are typically constructed of one or more elastomeric materials, or incorporate a composite structure including both elastomeric and non-elastomeric materials. Conventional elastic bandages, however, are not self-adhesive and tend to shift during and after application, thereby compromising the degree of comfort and compression that can be maintained. Such wraps are also clumsy and difficult to properly self-apply and are not suitable for one-handed application when conditions dictate the victim must provide self-aid. Such wraps also lack absorbent qualities and are not configured in a way that allows for the treatment of a wide range of injuries.

There is, thus, a widely recognized need for, and it would be highly advantageous to have wound dressings and wound dressing systems that provide for rapid and effective deployment for controlling bleeding that are not subject to the limitations of conventional wound dressings and wound dressing systems.

SUMMARY OF THE INVENTION

According to one aspect of the present invention there is provided a compression dressing, comprising a self-adhering elastic bandage designed and configured for exerting a compressive force when wrapped around a body part sufficient to hold the compression dressing in place for a therapeutic period of time; a pass-through structure, which, in some embodiments, can be reinforced, provided at a proximal end of the elastic bandage being arranged and configured whereby a distal portion of the elastic bandage may be deployed through the pass-through structure; and an absorbent pad being removably attached to an inner surface of the compression dressing.

According to another aspect of the present invention, the absorbent pad is removably attached to a support surface provided on the pass-through structure.

According to another aspect of the present invention, the pass-through structure and/or the support surface provided on the pass-through structure, are constructed of material(s) that exhibit flexibility sufficient to improve the correspondence between the surface contour of the injured limb and/or body part and the compression dressing, while limiting or reducing any stretching and/or deformation of the pass-through structure, e.g., KYDEX® or other suitable polymer, ballistic fabric, metal, or material or composite material capable of providing the desired combination of strength, flexibility, and dimensional stability. As will be appreciated by those skilled in the art, the material selected will typically maintain suitable physical properties across a wide range of temperature and humidity/moisture and will not become softened and/or embrittled under conditions present in anticipated use environments and may, or may not, be certified as a medical grade material.

According to another aspect of the present invention, the pass-through structure, wrap, or terminal end of the bandage includes a notation area suitable for application and retention of graphite or ink notations provided by the initial emergency care providers for the benefit of subsequent care providers.

According to another aspect of the present invention, the pass-through structure, wrap, or terminal end of the bandage includes a recessed area suitable for insertion and retention of a limited number of documents provided by the initial emergency care providers for the benefit of subsequent care providers.

According to another aspect of the present invention, the support surface is configured to be clear or translucent, thereby allowing for inspection of the condition of the underlying absorbent pad without necessitating partial or complete removal of the compression dressing.

According to another aspect of the present invention, the absorbent pad is arranged and configured to be removed, partially removed, or not removed, based on user preference from the compression dressing and opened to form a pouch or bag suitable for covering, padding, and/or protecting a limb stump remaining after an amputation. The bag or pouch can then be easily attached or secured around the limb stump that remains by an aid provider or the victim, using only one-hand if necessary.

According to another aspect of the present invention, the absorbent pad is arranged and configured to be removed, completely or partially, should the user desire, from the compression dressing and rolled, wadded, folded, or bunched to form an absorbent mass suitable for wound packing, wound protection, wound padding, or to create external compression of a desired area near or on a wound. The compression dressing with the pad removed may also be used for simple compression, stabilization, bandage extension, or as desired by a user skilled in the art.

According to another aspect of the present invention, the absorbent pad and/or the compression wrap is provided with one or more recesses or pockets into which designated or found objects, e.g., stones, cartridges, wadded gauze may be placed for providing increased pressure under at least a portion of the compression dressing. The addition of an object to the bandage is situated in a manner that a user skilled in the art may be able to generate additional point pressure where desired.

According to another aspect of the present invention there is provided a method for deploying the compression dressing in a rapid and effective manner under conditions of high stress such as military combat and/or limited space such as an aircraft or vehicle and if necessary by self-application using only one-hand, the method comprising placing the absorbent pad over the wound letting the pass through region hang or lie beyond the wound, unrolling a first portion of the elastic bandage around the injured body part in a first wrapping direction, passing a remaining portion of the elastic bandage through the reinforced pass through region, initially tensioning the bandage by pulling the remaining elastic bandage back over the initial wrap in the opposite direction of the first wrapping direction, continuing the application by unrolling a second portion of the elastic bandage in a second wrapping direction, the second wrapping direction being opposite the first direction and of the same direction as the tension was initially pulled, tensioning as desired with each subsequent wrap, and securing the second portion of the elastic bandage.

According to yet another aspect of the present invention there is provided a method of applying the compression dressing for treating "entrance-exit" or "through and through" wounds, the method comprising positioning the absorbent pad over one of the wounds; applying one or more additional absorbent pad(s) over the second, opposite wound; and wrapping the body part with one, or a linked plurality providing sufficient length, of the compression dressings in order to apply compression to the corresponding wounds on opposite sides of the injured body part. If indicated, a user skilled in the art may substitute a material suitable for use as a chest seal, such as the plastic bandage wrapper or engineered medical device to seal both the entrance and exit wounds in place of, or in conjunction with, the absorbent pad.

According to another aspect of the present invention there is provided a method of applying the compression dressing for treating evisceration wounds, the method comprising positioning the absorbent pad over the wound; applying one or more additional absorbent pad(s) if necessary and wrapping the torso with one, or a linked plurality providing sufficient length, of the compression dressings in order to effectively secure the bandage to prevent further disembowelment. If indicated, a user skilled in the art may use the absorbent pad, absorbent pad configured as a pouch or bag for primary use as a stump dressing, or the plastic bandage wrapper to cover, protect, seal, hold, and/or hold in the bowels.

According to still further features in some embodiments, the self-adhering elastic bandage strip is selected having self-adherence properties so as to allow unrolling of a roll of the elastic bandage strip without significant elastic extension of the elastic bandage strip.

According to yet further features in some embodiments, the self-adhering elastic bandage is constructed so as to have self-adhesive properties sufficient to prevent premature unrolling of the elastic bandage while still allowing the single-handed separation of adjacent layers of the elastic bandage as it is being deployed.

According to yet further features in some embodiments, the self-adhering elastic bandage is constructed whereby the self-adhering property is provided by an adhesive material provided as a pattern on at least one primary surface of the elastic bandage.

According to yet further features in some embodiments, the self-adhering elastic bandage is constructed whereby the self-adhering property retains its characteristics over a broad temperature range.

According to yet further features in some embodiments, the self-adhering elastic bandage is constructed so as to have self-adhesive properties sufficient to cause two adjacent layers of the compression dressing to remain adhered to one another under elastic extension without the use of a fastening mechanism.

According to yet further features in some embodiments, the self-adhering elastic bandage is constructed whereby the self-adhering property allows the user to re-roll the elastic wrap and retain enough adhesion that it will not unroll on its own, but still allow single-handed separation of the layers of the material when it is re-deployed.

According to yet further features in some embodiments, the self-adhering elastic bandage is constructed whereby the self-adhering property allows for the material to stretch with the elastic wrap and adhere to the previous and additional follow-on wraps to prevent pulled tension of the bandage from being released until desired.

According to yet further features in some embodiments, the self-adhering elastic bandage is constructed whereby the self-adhering property is sufficient in adherence strength to hold the wraps in place, even under tension, and not inadvertently unwrap should the person applying the bandage let go of the bandage before it is properly secured.

According to further features in some embodiments, the self-adhering elastic bandage strip is constructed of a transparent or translucent material.

According to further features in some embodiments, the self-adhesive elastic strip is constructed of clear polyolefin polymer and/or heteropolymer films coated with an extendable, self-adhesive coating or pattern providing sufficient coverage and tack strength to permit adjacent layers of the bandage to remain adhered to one another while under tension without the use of a separate fastening mechanism.

According to yet further features in some embodiments, the self-adhering elastic bandage is constructed whereby premature deployment is suppressed by tack-stitching of the adjacent layers of the elastic bandage.

According to yet further features in some embodiments, the self-adhering elastic bandage is constructed whereby premature deployment is suppressed using patches of hook and loop fasteners or other complementary fastening surfaces on the adjacent layers of the elastic bandage. According to further features in preferred embodiments of the invention described below, the absorbent pad is removably attached to the compression dressing by stitching, welding, tack-stitching, needle-tacking, adhesives, hook and loop fasteners, and/or bonding.

According to further features in preferred embodiments of the invention described below, the absorbent pad is constructed of foamed, woven, and/or nonwoven material of natural and/or synthetic fibers selected from the group consisting of rayon, polyester, polyurethane, polyolefin, cellulose, cellulose derivatives, cotton, orlon, polymeric hydrogels, and mixtures and combinations thereof.

According to still further features in some embodiments, the absorbent pad includes a coagulant and/or an antibiotic/ antimicrobial substance.

According to further features in preferred embodiments of the invention described below, the compression dressing is rolled into a roll or folded into a pad of varying sizes and shapes, and packaged in a sterile or non-sterile package. The bandage may be compressed and/or vacuum sealed to minimize the overall size of the packaged device.

The present invention addresses and overcomes certain aspects of the known shortcomings of the conventional compression dressing configurations by providing a self-adhering elastic compression dressing having a variable sized and removable absorbent/protective surface(s) that is reconfigurable to the nature of the wound while providing adequate and adjustable compression using a novel design incorporating a pass-through piece that enables simple, rapid, and effective deployment of the compressing dressing over a range of injured body parts in a manner suitable for both one-handed self-aid and/or traditional application by an aid provider. The simplicity inherent in this invention makes it suitable for use in high-stress situations such as military combat. Further, the dressing of the present invention requires limited extension during deployment and is, therefore, suitable for use in confined spaces such as vehicles and aircraft.

According to one aspect of the present invention there is provided a compression dressing system or kit, comprising a self-adhering elastic bandage; a reinforced pass-through structure; and an absorbent pad being removably attached to an inner surface of the compression dressing all sealed in a sterile or non-sterile, fluid and/or gas impermeable package.

According to further features in preferred embodiments of the invention described below, the sterile package is arranged and configured to be opened to form a pouch suitable for covering and protecting a limb stump remaining after a traumatic amputation, sealing abdominal wounds, sealing thoracic wounds (e.g., pneumothorax) and/or for collecting residual body parts for transport with the injured person.

BRIEF DESCRIPTION OF THE DRAWINGS

The invention is herein described, by way of example only with reference to the accompanying drawings. With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention and the drawings are not to scale. The description, when considered in light of the drawings, are believed sufficient to permit those of at least ordinary skill in the art how the several forms of the invention may be embodied in practice without undue experimentation.

DETAILED DESCRIPTION

Figures 1A, 1B:
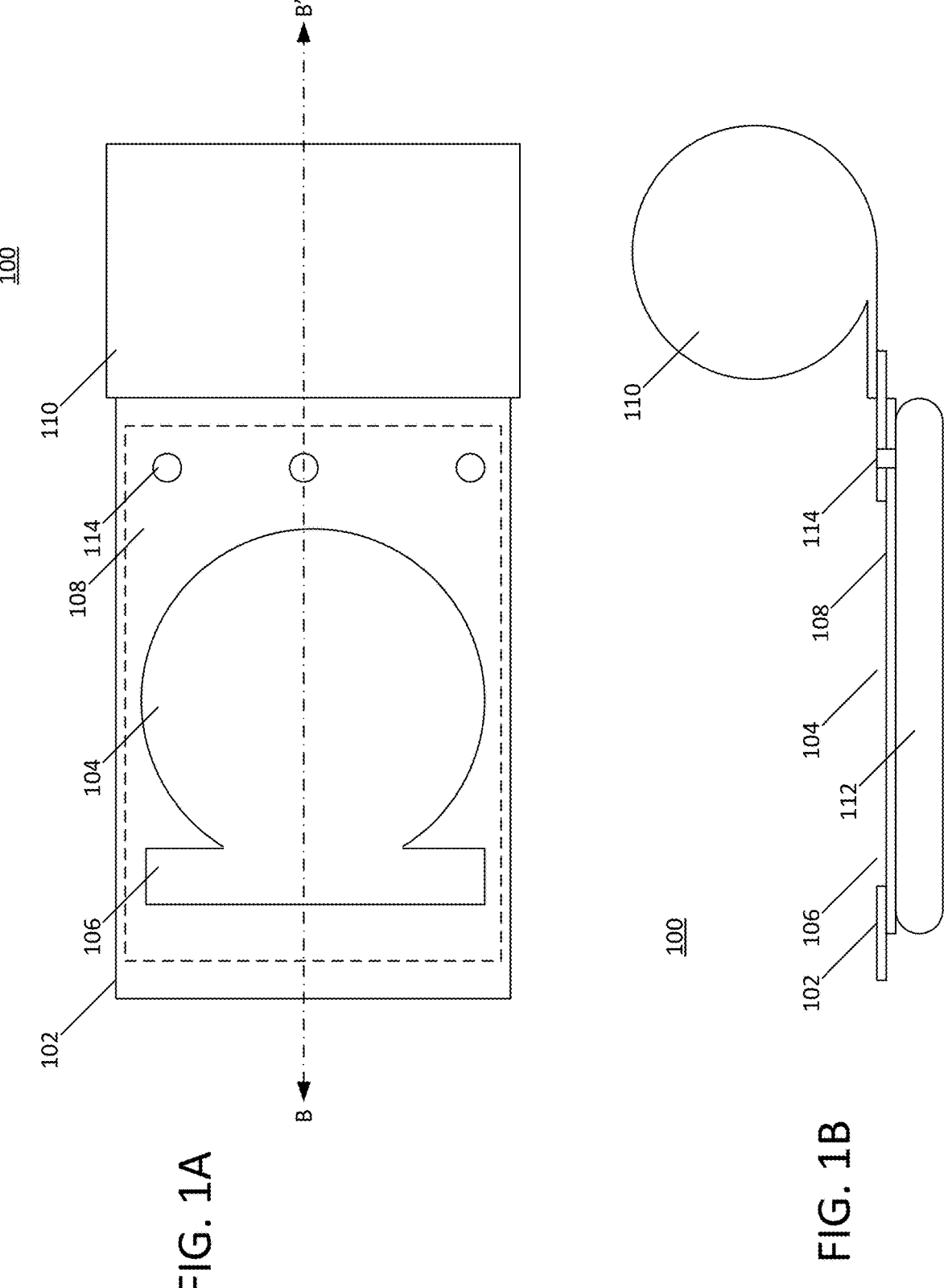
FIGS. 1A and 1B illustrate an embodiment of the enhanced trauma bandage with FIG. 1B being a cross-sectional view of FIG. 1A taken along line B-B'.

The Enhanced Trauma Bandage (ETB) comprises several embodiments of compression dressings and elastic bandages engineered and configured for use in trauma dressing applications. Each of the ETB embodiments includes at least a resilient elastic wrap, at least one dressing (e.g., a sterile, non-adherent), and a reinforced pass-through region. This combination of elements allows for the rapid, controlled, and effective application of the ETB to a wound or limb under even challenging environmental or lighting conditions and/or one-handed self-application. The design is meant to be simple and provide gross tactile feedback so that even an individual under extreme stress, wearing gloves, and/or operating in a no or low-light environment can rapidly and effectively apply the bandage. As explained in more detail below, the basic ETB may be combined with other elements and/or modified to include other features that increase the utility and/or provide for different wound treatment modes.

When properly applied by those skilled in the art, the ETB is extremely adaptable and can protect the wound, provide compression to prevent or suppress blood loss, absorb fluids, allow for wound packing, support an injured limb, seal a thoracic wound, and/or protect the limb stump in the case of an amputation. As will be appreciated by those skilled in the art, a range of dressings may be used in combination with the ETB. When configured as part of a kit, two or more types of dressings may be included with the ETB with the types of dressings selected based on the anticipated injury mechanisms and causes.

Generally, traditional dressings are indicated for use only with superficial, clean, and dry wounds with minimal exudates. They can also be used as secondary dressings and may include a variety of natural and/or synthetic fibers. The main purpose of such dressings is protecting the wound from (additional) bacterial contamination although they can also be used for secondary dressings.

Semi-permeable film dressings comprise a polymeric film that allows the movement of water vapor, oxygen, and carbon dioxide both into and out of the dressing. It also plays an additional role in autolytic debridement (removal of dead tissue) which is less painful when compared to manual wound debridement. These dressings are highly elastic and flexible; thus, are closely adhered to the skin. As the dressings are typically transparent, wound inspection is possible without removing the dressing. However, due to the limited absorption capacity, such dressings are typically only used in treating superficial wounds with low amounts of discharge.

Semi-permeable foam dressings comprise an inner hydrophilic foam layer and an outer layer of hydrophobic film, typically with adhesive borders. The hydrophobic layer protects the wound from the outside fluid contamination while the inner hydrophilic layer absorbs discharge from the wound. Therefore, this type of dressing is useful for wounds with high amounts of discharge.

Hydrogel dressings are formed from synthetic polymers such as methacrylate and polyvinylpyrrolidine and, relative to other dressings, have a relatively high water content; thus, providing moisture and cooling for the wound. These dressings are typically more easily removed from the wound without causing any additional damage. These dressings also tend to be non-irritating and are more commonly used in the treatment of dry necrotic wounds, necrotic wounds, pressure ulcers, and burn wounds.

Hydrocolloid dressings include an inner colloidal layer and outer waterproof layer. The inner layer typically contains gel forming agents such as carboxymethylcellulose, gelatin, and/or pectin. When these dressings are in contact with a wound, the wound discharge is retained to form gel while providing a moist environment for wound healing. This protects the wound from bacterial contamination, absorbs wound discharge, and reduces necrotic tissues.

Alginate dressings include either the sodium or calcium salt of alginic acid and can absorb high amounts of discharge from a wound. Ions present in the dressings can also interact with blood or other discharge to produce a protective film to prevent or reduce further bacterial contamination.

Although there are a number field dressing and/or emergency bandage commercially available, the existing options are not well-configured for one-handed/self-application situations, require training (and repeated retraining) for proper and rapid deployment, unravel/unroll inadvertently, and may include plastic parts that can break under load and/or become embrittled as a result of exposure to heat/cold during storage or use. These rigid parts also add bulk, size, and weight to basic elements of the ETB and, depending on the dimensions, can prevent the ETB kits that are supplemented in this manner from being packaged in shapes and sizes most convenient and/or advantageous for the user.

The ETB embodiments disclosed herein, however, are configured to allow true one-handed application even while wearing gloves and/or under low to no-light conditions. The primary dressing may also be configured for full or partial removal to provide for the substitution of a more appropriate dressing and/or to use the removed portion of the dressing for wound packing. The primary ETB dressing may also come in a configuration that allows it to be expanded as a standalone bag/pouch or stuffed into a bag that can then be used for encapsulating, covering, and/or protecting the stump remaining after an amputation and/or to reduce contamination of an amputated body part during transport to a medical facility. This ETB configuration gives a marked advantage over other dressings for amputations because of its extreme simplicity of use and ability to securely fasten it around a limb. The procedures for applying the ETB embodiments disclosed herein are fairly intuitive so the associated instruction time can be relatively brief and tends not to need to be repeated with any great frequency to maintain proficiency.

A basic configuration of the ETB 100 is shown below in FIG. 1A, a plan view, and FIG. 1B, a cross-sectional view along line B-B'. The ETB includes a reinforced pass-through region 102, in which a pass-through opening 104 and a connected tensioning opening 106 are provided. A dressing support surface 108 can be provided below, and attached to using attachments 114, the reinforced pass-through region 102 for attaching/supporting the dressing 112.

The dressing 112 may be any variety of absorbent material such as gauze and may be a pad, folded strip, pouch, and/or other configuration and may be impregnated or treated with anti-microbial compounds and/or hemostatic (clotting) agents designed to suppress and stop hemorrhaging. The reinforced pass-through region may be in various configurations designed to support and accommodate a range of shapes of the rolled or stacked material to be easily passed through. The reinforced pass-through region may include an appropriately sized ring, D-ring, eyelet, and/or other structure suitable for use as the pass-through area instead of a reinforced hole.

The tensioning opening 106 is designed to prevent or reduce bunching of the wrap, which allows for a more even and smooth application of the bandage wrap. Suppressing the wrap's tendency to bunch will reduce the formation of rope-like bunched fabric that can interfere with the typically preferred even application of a compression bandage. This slotted area corrects this problem found in other bandages. Tensioning opening 106 may be linear, V-shaped, or curved in order to better accommodate spreading the ETB bandage material to its natural width. A roll, bundle, or folded stack of bandage material 110 is attached to the pass-through region opposite the tensioning opening. In some embodiments, the dressing support surface may be transparent or translucent so that the condition of the underlying dressing may be evaluated without reducing the pressure being applied to the wound.

The pass-through region and/or the dressing support surface may be provided with one or more pockets (not shown), into which, or attachment areas (not shown), onto which, additional materials including, for example, rocks, lighters, casings, sticks, and other suitable objects, may be placed to provide additional point pressure on or adjacent the wound being treated to reduce or stop blood loss.

The bandage material 110 may be configured and manufactured to provide a desired degree of self-tack sufficient to allow the roll to maintain its integrity until deliberately unrolled as the ETB is being applied. If the material of the bandage itself does not exhibit a sufficient degree of tack, a pattern of adhesive lines, dots, or other patterns, may be applied to one or both main surfaces of the bandage to achieve the same effect. This self-tacking feature has the added benefits holding the ETB bandage in place during application, preventing slippage of the bandage once applied, and maintaining an increasing amount of pressure with each wrap. If the bandage is packaged in a flat folded configuration, tack stitching may also be used to prevent inadvertent or premature deployment.

Although shown as separate elements, the pass-through region 102, the dressing support surface 108, and the bandage material 110 are shown as illustrated as distinct elements for the sake of convenience. Those skilled in the art will appreciate that one or more of these elements can be executed in combination. For example, an initial portion of the bandage material 110 may be provided with structural reinforcement suitable for suppressing or eliminating significant deformation of the pass-through region and the associated openings during use. Similarly, the backside of the initial portion of the bandage may be provided with adhesive regions or other suitable elements for providing a removable attachment of the dressing 112 without the necessity of a separate dressing support surface 108.

Figure 2A:
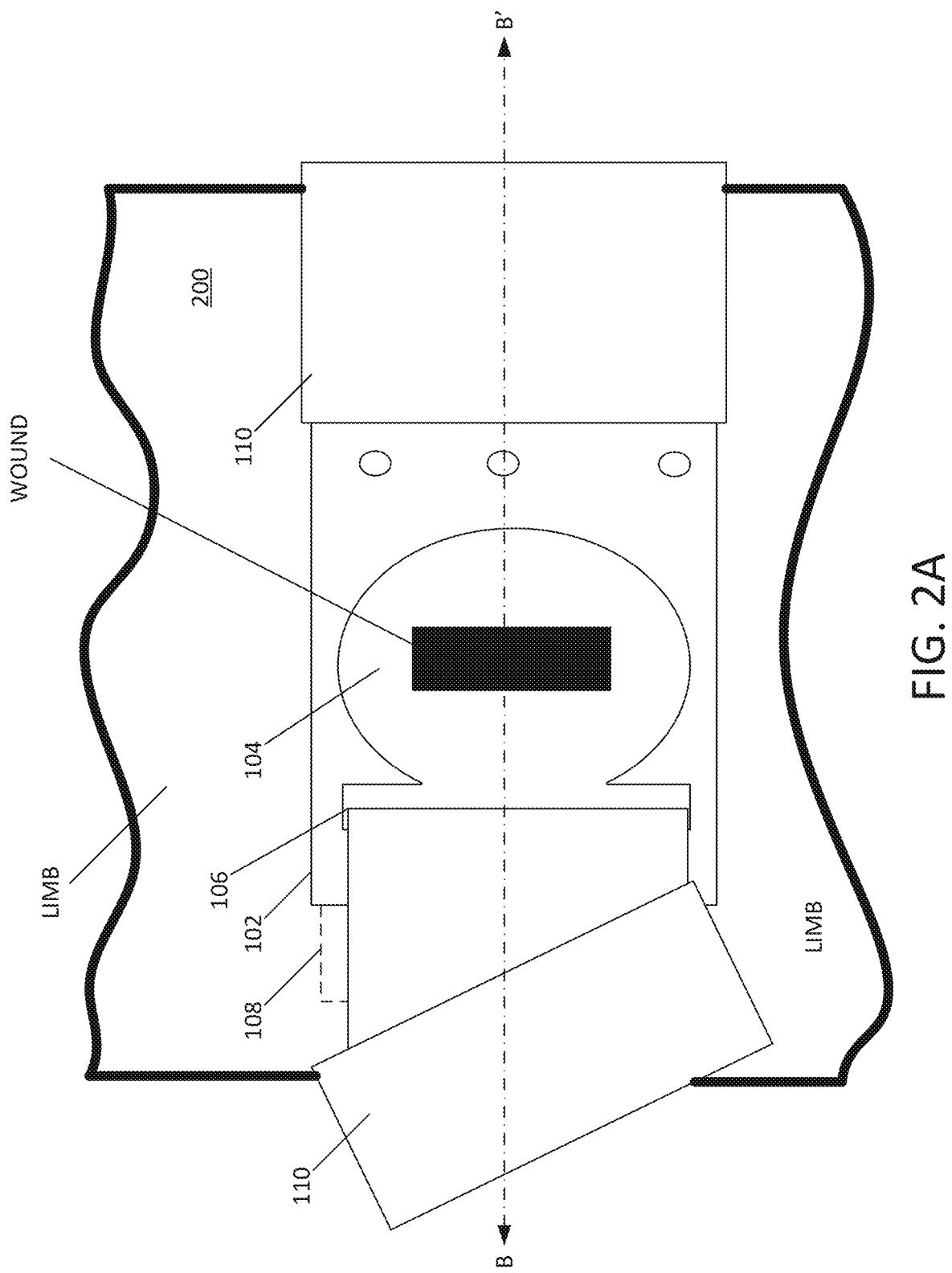
FIG. 2A illustrates an embodiment of the enhanced trauma bandage being deployed on an injured limb.
Figure 2B:
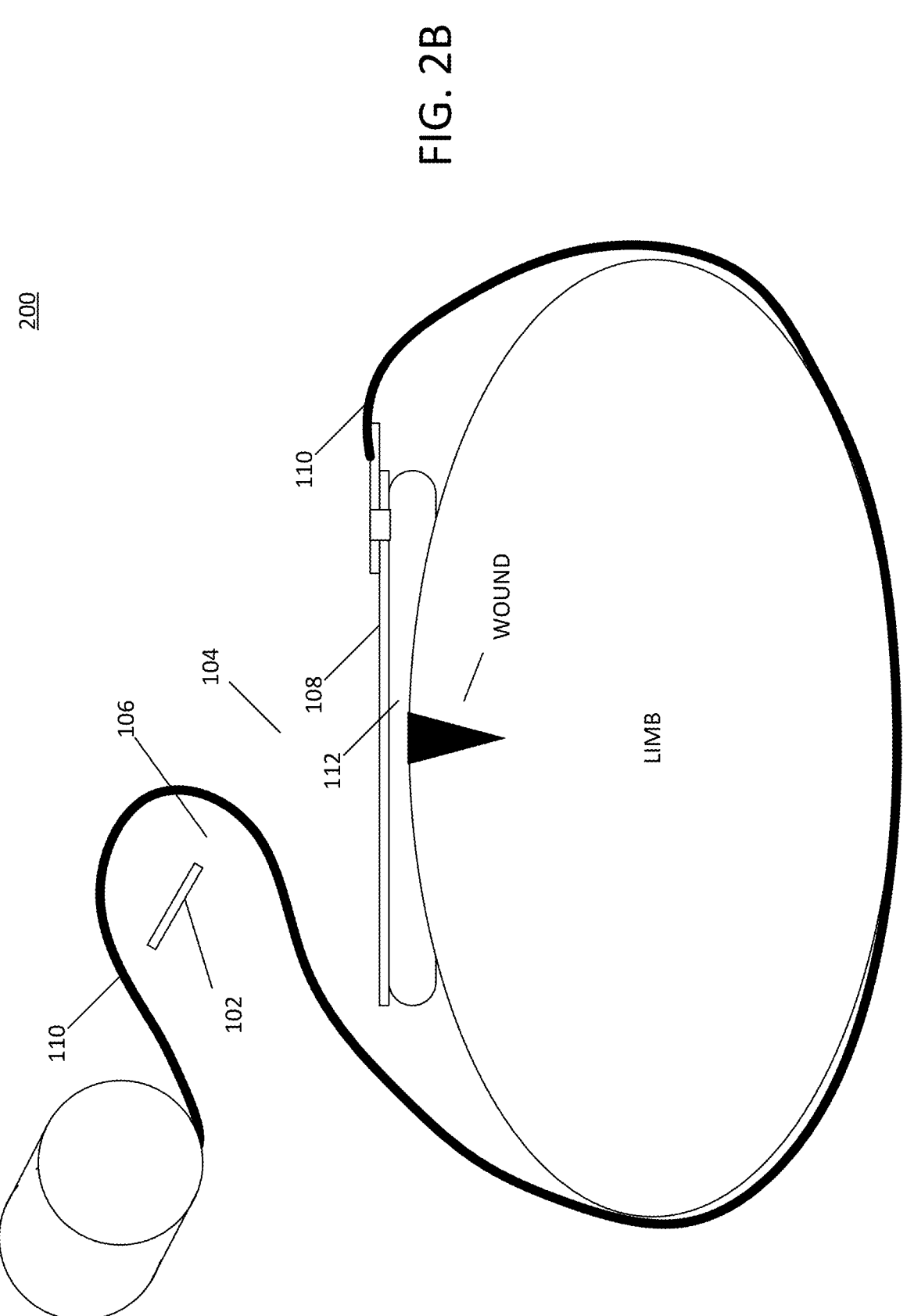
FIG. 2B illustrates an intermediate step of the deployment in a cross-sectional view of FIG. 2A taken along line B-B'.
Figure 2C:
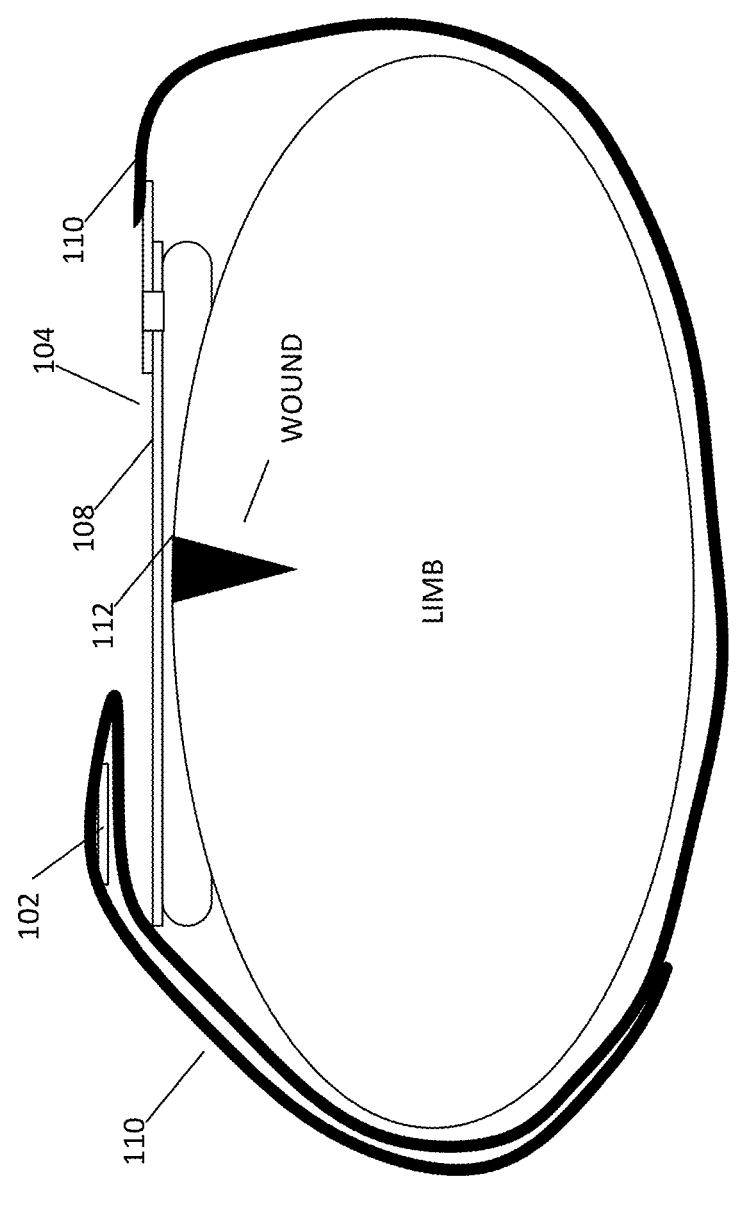
FIG. 2C illustrates a final step of the deployment in a cross-sectional view of FIG. 2A taken along line B-B'.

An initial application of the basic ETB to an injured limb is illustrated in FIGS. 2A and 2B, which generally correspond to the pre-deployment configuration illustrated in FIGS. 1A and 1B. As illustrated in FIG. 2A, the ETB has been placed on the surface of an injured limb and the bandage roll 110 has been brought through the pass-through opening 104 as it is unwrapped/unrolled/unfolded, with a portion of the bandage then being pulled into tensioning opening 106 to allow the bandage to evenly spread to its natural width. At this point, the wrapping direction is reversed over the previously applied portion of the bandage. This allows the bandage to be pulled snug against the tensioning opening, thereby securing the dressing 112 against the wound (not shown) and applying the initial tension to the dressing. Each successive wrap of the bandage around the wound can increase pressure and/or provide greater coverage and protection of the wound area. The ETB design disclosed herein enables the bandage to be applied using one or two hands and can either be self-applied or applied by an aid provider to any limb or even to the torso.

The same initial application of the basic ETB to an injured limb is shown in cross-section in FIG. 2B. Because in this embodiment the reinforced pass-through region I 02 is attached to the dressing support surface 108 at only the edge adjacent the bandage attachment, the pass-through region may be lifted or tilted relative to the remainder of the assembly to increase the ease with which the bandage may be pass-through opening 104.

Once the wrapped direction has been reversed as illustrated in FIG. 2B, the bandage may be wrapped at least partially or multiple times as desired and permitted by the particular ETB embodiment in order to apply the dressing around the injured limb or wound. The ETB is then secured in a manner sufficient to maintain the established level of compression over the wound as illustrated in below in FIG. 3.

A section of material containing a pocket or pockets configured for receiving field-expedient (e.g., stones, coins, gum, pens, cartridges, or other readily available objects) or prepared point pressure device(s) (not shown) may then be adjusted over the dressing 112 so that any subsequent wraps placed over the pocket containing the point pressure device will deliver increased point pressure to at least a portion of the wound site to which the ETB is being applied. The free end of the bandage may then be secured by simply tucking or tying the loose end or with suitable prongs, clips, or other attachment means (not shown) sufficient for securing at least the top two layers of the bandage to each other in order to maintain the compression and prevent unraveling.

In addition to maintaining the roll integrity, the self-tack or adhesive patterns added to the surface(s) of the bandage also assists in maintaining compression of the applied ETB and suppress unraveling. The ETB may be provided in multiple lengths, widths, and materials intended for application to and treatment of a variety of traumatic wounds.

Because each of the ETBs include a pass-through region 102, two or more ETBs may be easily and effectively joined end-to-end if necessary to provide a longer bandage for treatment of, for example, a thoracic wound. And because, at least in some embodiments, there are no rigid elements incorporated into the ETB, it may be folded and/or compressed for storage in a relatively small pack or canister or as desired by the user.

As noted above, the dressing may be removably attached, or separate, from the rest of the ETB to provide maximum utility and modularity to the bandage. Accordingly, an ETB pack may include multiple dressing options intended to provide one or more functions including, for example, stopping or controlling bleeding by sealing the wound and/or expediting the clotting process with or without hemostatic agents; reducing the chance of infection by protecting the wound from additional environmental contamination, applying an anti-microbial compound and/or reducing further mechanical damage; absorbing fluids from the wound including blood, plasma, and/or other fluids; reducing pain through the application of an analgesic, compression, and/or stabilization of the wound field; debriding the wound; and/or reducing stress by obscuring the severity of the injury.

As will be appreciated by those skilled in the art, the pass-through region 102 included in the ETB may utilize a wide range of configurations and materials for maintaining the basic structural and dimensional stability of the pass-through region during application of the ETB. This result may be achieved by layering materials or by modifying that portion of the ETB with reinforcing fibers, laminates, coatings, or other structures that will provide additional strength, tear resistance, and/or dimensional stability.

The pass-through opening 104 should be sized to allow for remaining portion of the bandage roll 110 to be passed through the opening without difficulty. The tensioning opening 106 should be sized and configured to help maintain substantially the full width of the bandage and may therefore be arranged as a linear opening (shown) or as a curved or angled opening that will tend to help spread the portion of the bandage passing through the opening. For example, a curved opening in which the sides are farther from the pass-through opening promotes the even spreading of the elastic compression wrap and prevents bunching when the roll is passed through and the wrap pulled back on itself to tighten bandage Various elements of the ETB may be attached using a plurality of discrete attachments 114 that may comprise rivets, adhesives, stitching, plastic welding, and/or any other suitable means of securely attaching the various materials to one another. Conversely, the dressing, if attached at all, will be attached below the pass-through region in a manner that allows for its easy removal and modification including, for example, balling the dressing to provide improved wound packing, folding the dressing to increase its effective thickness, and application of various medicaments and/or clotting factors to the dressing. For example, although wound packing is generally contraindicated for severe neck wounds, the dressing could be pulled free at the corners and folded to make a tight ball under the pass-through region that can be used to provide additional compression where a basic gauze dressing is not sufficient.

In some embodiments of the ETB, the pass-through region may include more rigid elements such as cinch rings, either round, D-ring, or elongated, teeth, barbs, and/or prongs for improving the attachment of the bandage to the pass-through region. As noted above, the lower surface of the pass-through region 102 may include one or more pockets, flaps, hook-and-loop, or other regions configured for receiving a designed or improvised point pressure device. These pressure point devices permit the ETB to be reconfigured in the field for applying additional pressure for suppressing bleeding and/or maintaining positioning of wound packing. One or more point pressure devices may be included in the basic ETB pack, or may be improvised from pebbles, marbles, stones, lighters, spent cartridges, wads of paper, etc. depending on the number and size of pressure points needed and the materials immediately available for such use as the ETB is being applied.

The pouch or other region will typically be designed to maintain the orientation of the point pressure device during the wrapping. For example, the pouch or pocket may have an opening that may be secured with a snap, loop and hook surfaces, adhesives, or any other suitable means of securing the point pressure device within the pouch. As an alternative to the pouch or pocket, an adhesive region may be provided that is initially covered by a protective. release film. Removing the release film exposes the adhesive region and allows a point pressure device to be secured to the adhesive as the ETB is applied.

It is anticipated that for most applications, the ETB and any associated materials will be packed in a sterile pouch formed from a relatively impermeable film material to form a unitary ETB kit. Depending on the nature of the wound, the pouch itself may be used in the application of the ETB for the treatment of, for example, sealing a chest wound or perforated lung (sucking chest wound) or protecting eviscerated bowels.

Similarly, it is preferred that the pouch be sized or, in the alternative, be configured to be expandable, to form a pocket of sufficient size to fit over the remaining portion of an amputated limb. An expandable ETB pouch may include, for example, a primary region sized for holding the bandage and dressing (and any desired accessories) with a compressed, folded (e.g., using an accordion-fold method), or rolled portion that can be expanded to greatly increase the opening and volume of the pouch.

Figures 7A, 7B, 7C, 7D, 7E, 7F, 7G, 7H:
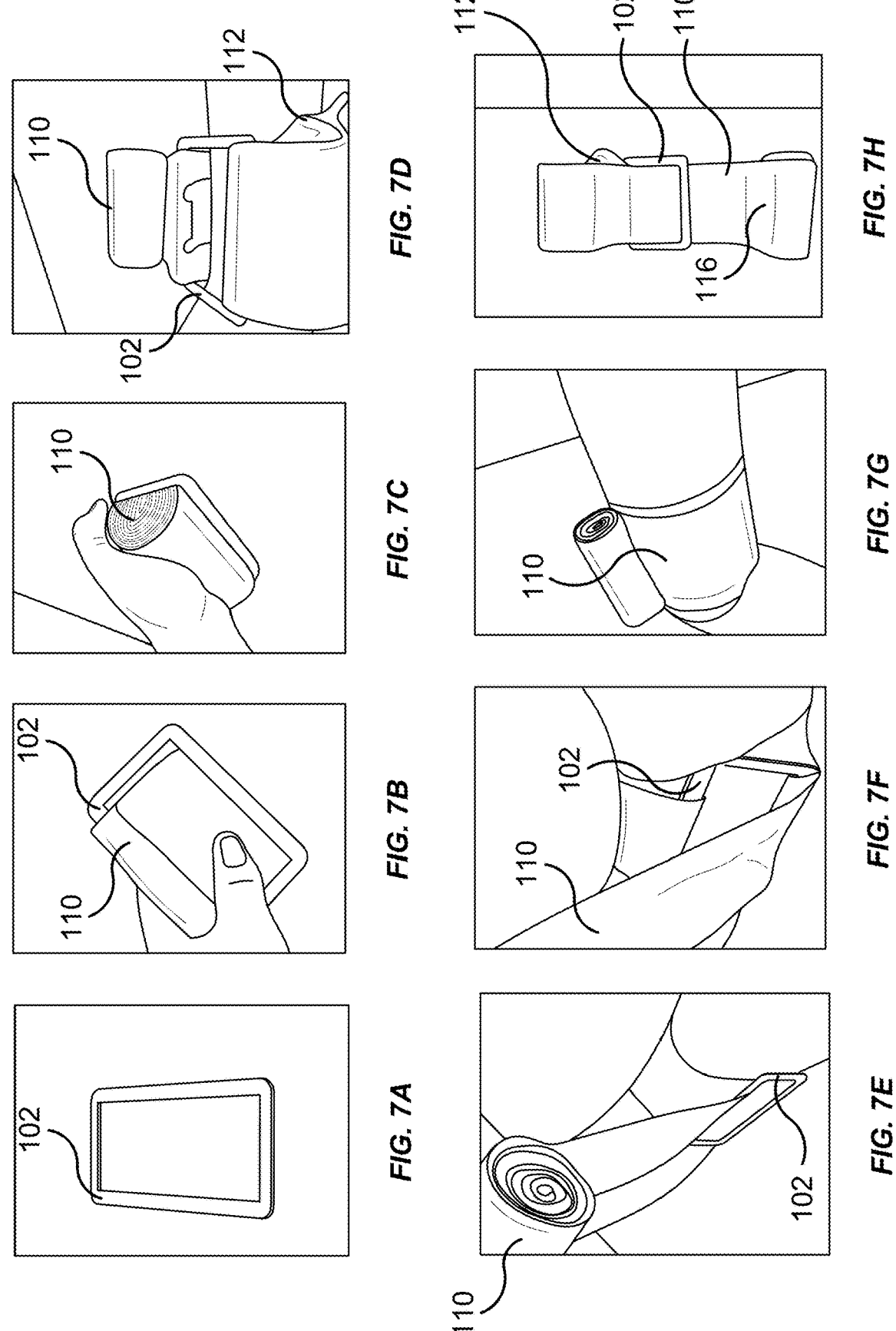
FIGS. 7A-7H illustrate a deployment sequence of an embodiment of the enhanced trauma bandage according to FIG. 5A around a limb.

As illustrated in FIGS. 7A-7H, the compression dressing may be applied to, for example, a wounded limb, by removing the compression dressing from its pouch or other container, FIGS. 7B-C, positioning the absorbent pad over a damaged portion of the wounded limb FIG. 7D; wrapping a first portion of the elastic bandage around the wounded limb in a first direction; passing a second portion of the elastic bandage through the pass-through region; tensioning the residual portion of the elastic bandage against the bandage guide structure FIG. 7E; wrapping the second portion of the elastic bandage around the wounded limb in a second direction, the second direction being opposite the first direction FIG. 7F-G; and securing a distal portion of the elastic bandage to maintain the compression dressing.

In some embodiments, particularly in the case of a traumatic amputation, a first portion of the ETB wrapping can be used to partially fill a portion of the pouch before the pouch is applied to the remaining portion of limb. A second portion of the ETB wrapping can be maintained external to the pouch and then used to secure the pouch to the remaining portion of the limb, thereby increasing the likelihood that the dressing will remain in place during transport. In some embodiments (not shown), a series of fabric or rope loops may be provided around the periphery of the opening of the pouch through which at least a portion of the ETB wrapping can be threaded to provide a more secure attachment. In some embodiments (not shown), one or more circumferential friction regions or structures may be provided around the periphery of the opening of the pouch for increasing the secure attachment of the material(s) being used to secure the pouch to the remaining portion of the limb. The friction regions/structures can also provide for more secure handling of the ETB, particularly when the ETB is being handled persons wearing gloves or other hand protection.

In addition to the ETB wrapping, the open end of the pouch can be secured using tape, elastic band(s), tie-downs, and/or another suitable closure device(s) to secure the pouch over the end of the injured limb. If an alternative means for securing the pouch is available, then the ETB wrapping can be applied to the limb and then covered by the pouch to reduce subsequent contamination of the wound and/or the wrapping. In those instances in which an ETB wrapping is used to secure the pouch, the dressing can be removed from the ETB and inserted into the pouch before being applied to the injured limb.

Figure 8C:
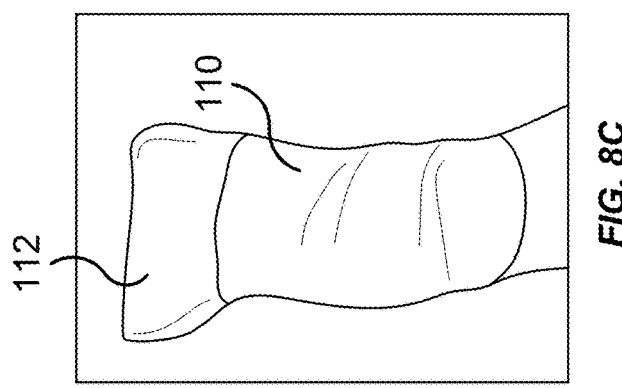
FIGS. 8A-8C illustrate a deployment sequence of an embodiment of the enhanced trauma bandage according to FIG. 5A around the stump of a limb after a traumatic amputation.
Figure 8B:
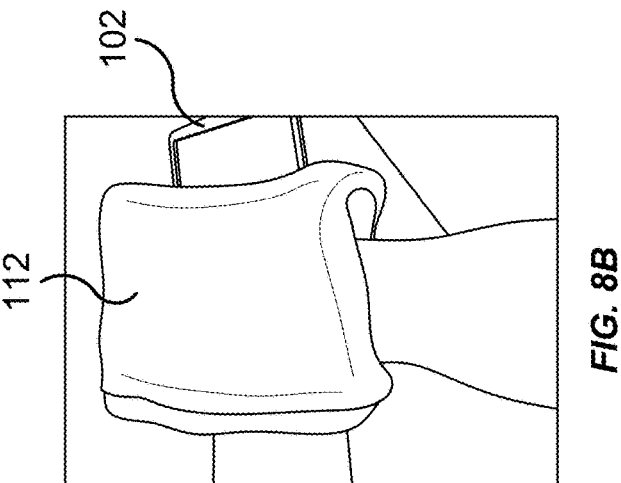
Figure 8A:
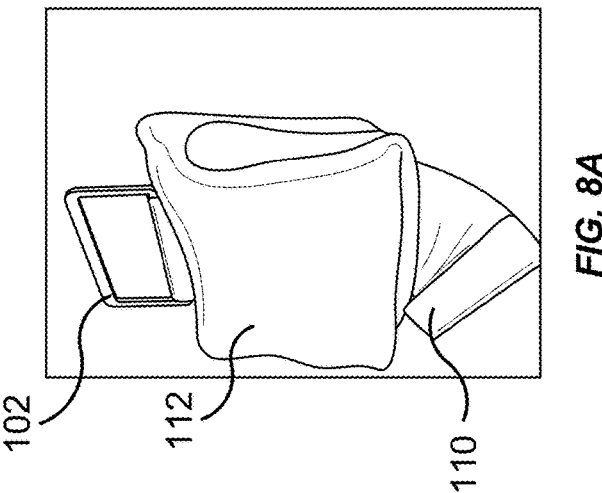
Figure 9:
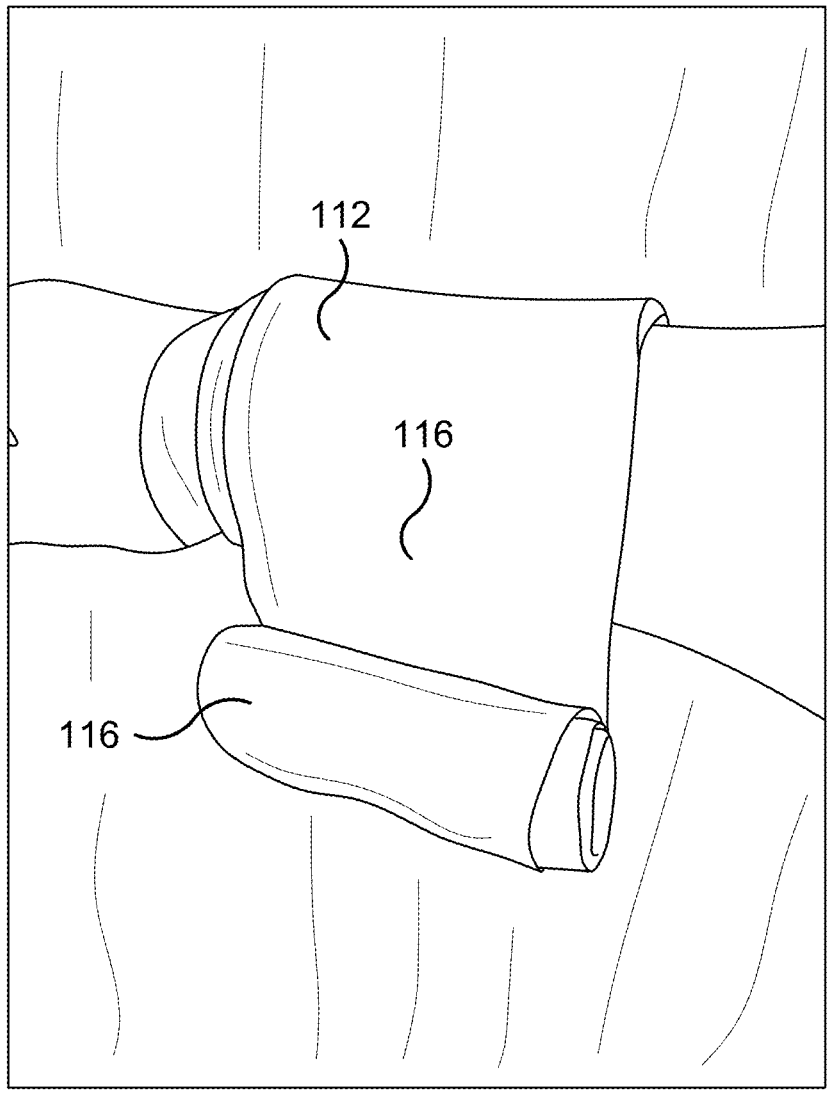
FIG. 9 illustrate an embodiment of the enhanced trauma bandage generally according to FIG. 5A in which a pattern of adhesive 116 is provided on at least one side of the bandage, the adhesive having sufficient tack to prevent the bandage from unrolling without involvement of an emergency care provider.

As will be appreciated by those skilled in the art, the ETB wrap and/or dressing may also be configured (e.g., may be in the form of an expandable pocket/pouch, folded, or multi-layered) so that a user can readily expand the wrap and/or dressing to, for example, cover the remaining portion of an amputated limb, provide additional coverage area for larger wounds, and/or be used to stuff an expanded pouch. In some embodiments, the ETB is configured with an expandable dressing pocket/pouch where the dressing may be compressed, formed, folded (e.g., using an accordion-fold method), or rolled so that it can be expanded to greatly increase the opening and volume of the pouch. The expanded dressing of the ETB being used as a pocket/pouch may then be easily placed over the end of an amputated limb, wrapped, and secured by those skilled in the art as shown in FIGS. 8A-C. By encapsulating the stump of an amputated limb with the ETB dressing, the injury is protected from further damage, additional contamination, and increased nerve sensitivity. The ability to easily secure the dressing to the stump increases the likelihood that the dressing will remain in place during transport, will not require adjustment, and will not cause additional aggravation of the injury.

Some embodiments of the ETB may include a wrap dispenser assembly attached to the pass-through region from which the bandage 110 may be unrolled during application. One advantage of this construction is that the size of the pass-through opening 104 may be reduced because only a free end of the bandage 110 will be passing through the opening as opposed to the remaining portion of the bandage when rolled with the free end in the center. The wrap dispenser assembly will typically be constructed from a strong lightweight material, such as a reinforced polymer, and will include a cylinder with the sleeve around which the bandage will rolled. The dispenser may be configured with a feed slot sized to provide some resistance to the unrolling of the bandage to prevent accidental, premature, or excessive unrolling, while still allowing for the bandage to be rewound onto the cylinder if desired. The feed slot may also be configured for establishing and maintaining tension to the bandage that will assist the user in ensuring that the bandage is being adequately stretched during the wrapping process which, in turn, enhances the likelihood of proper bandage application.

Figure 3:
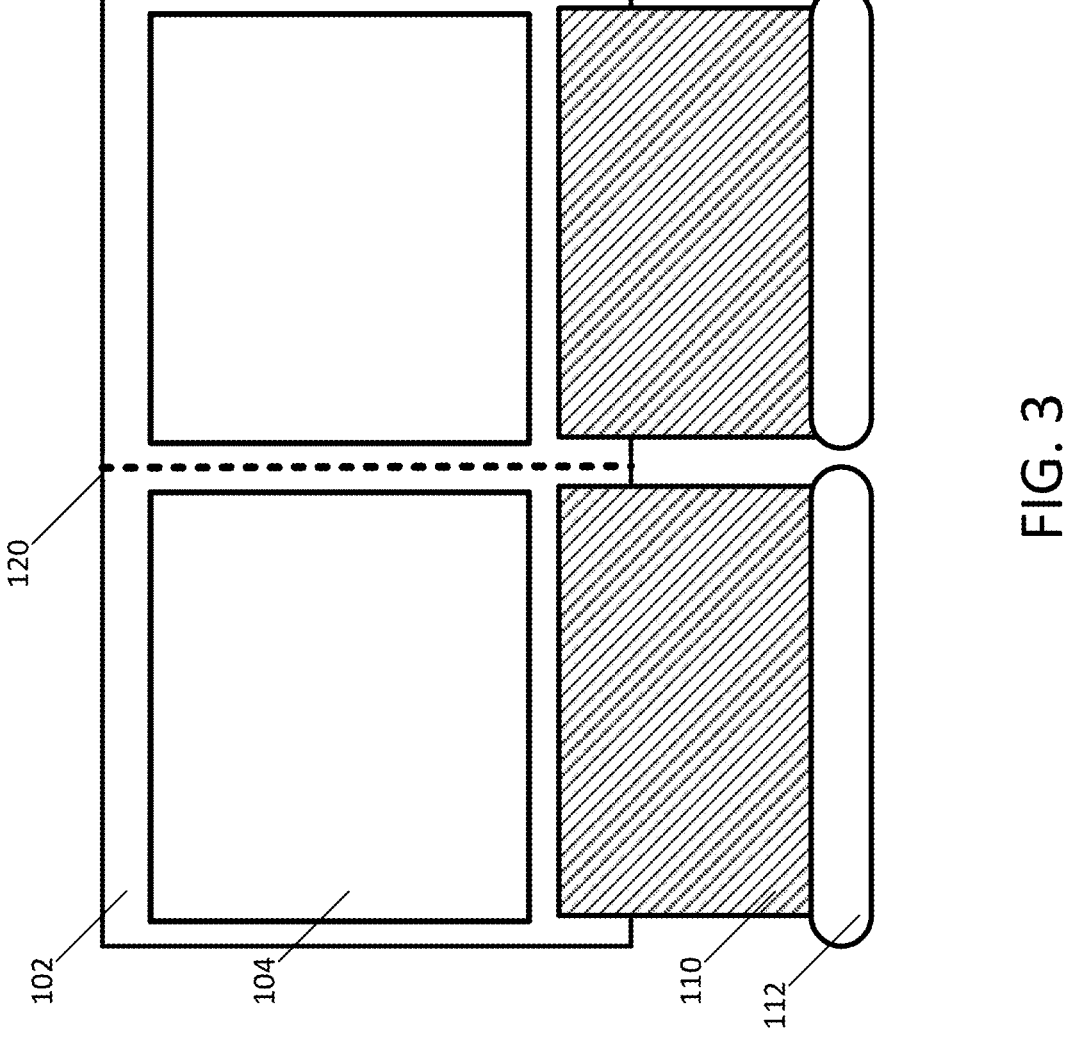
FIG. 3 illustrates an embodiment of the enhanced trauma bandage in which a pair of enhanced trauma bandages are joined along a severable joint 120 to allow for joint or separate deployment according to FIGS. 2A-2C.
Figures 4A, 4B, 4C:
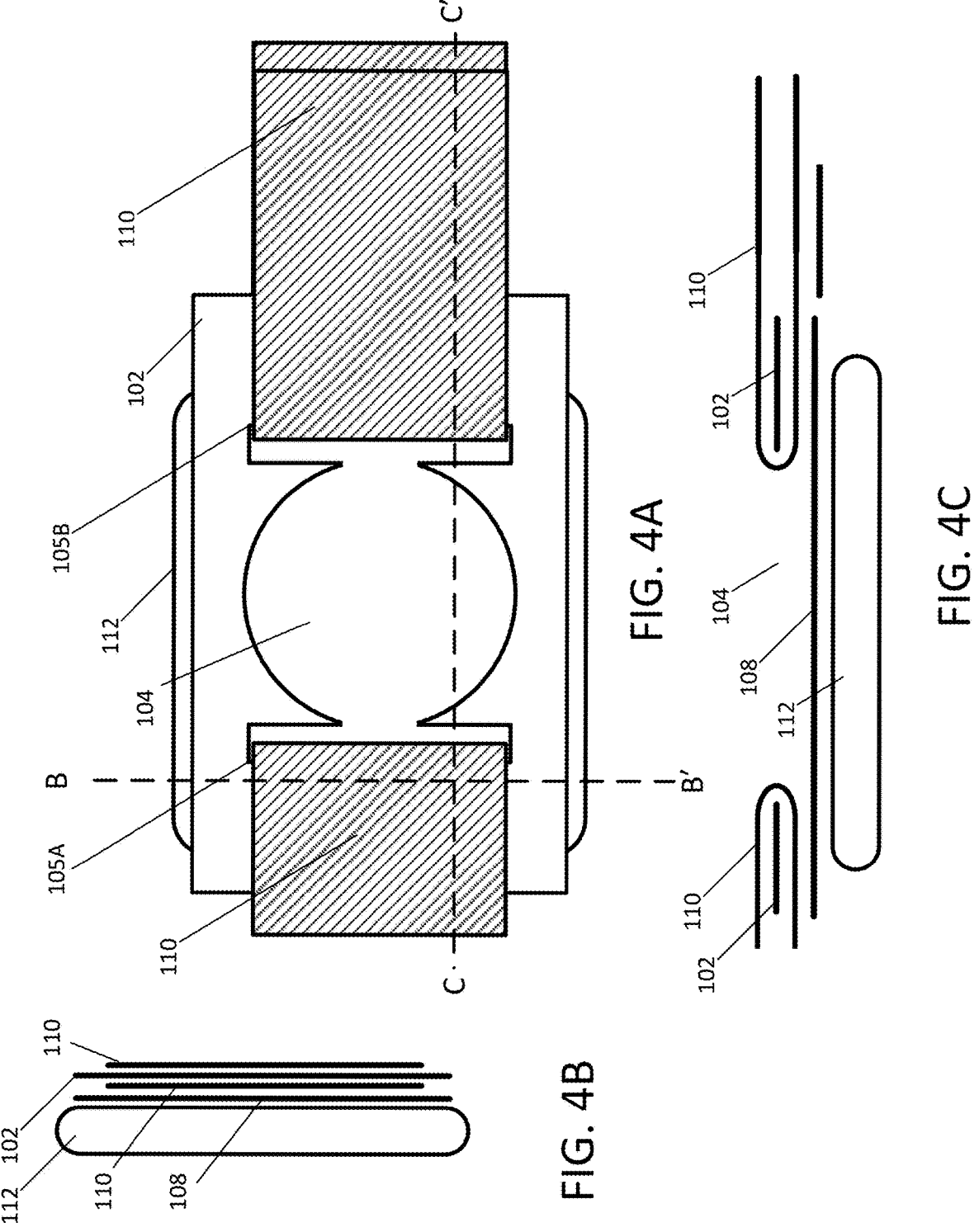
FIGS. 4A-4C illustrate an embodiment of the enhanced trauma bandage in which the reinforced pass-through region is modified to allow the bandage to be wrapped in a manner that does not obscure the pass-through region with FIG. 4B being a cross-sectional view of FIG. 4A along line B-B' and FIG. 4C being a cross-sectional view of FIG. 4A along line C-C'.
Figures 5A, 5B:
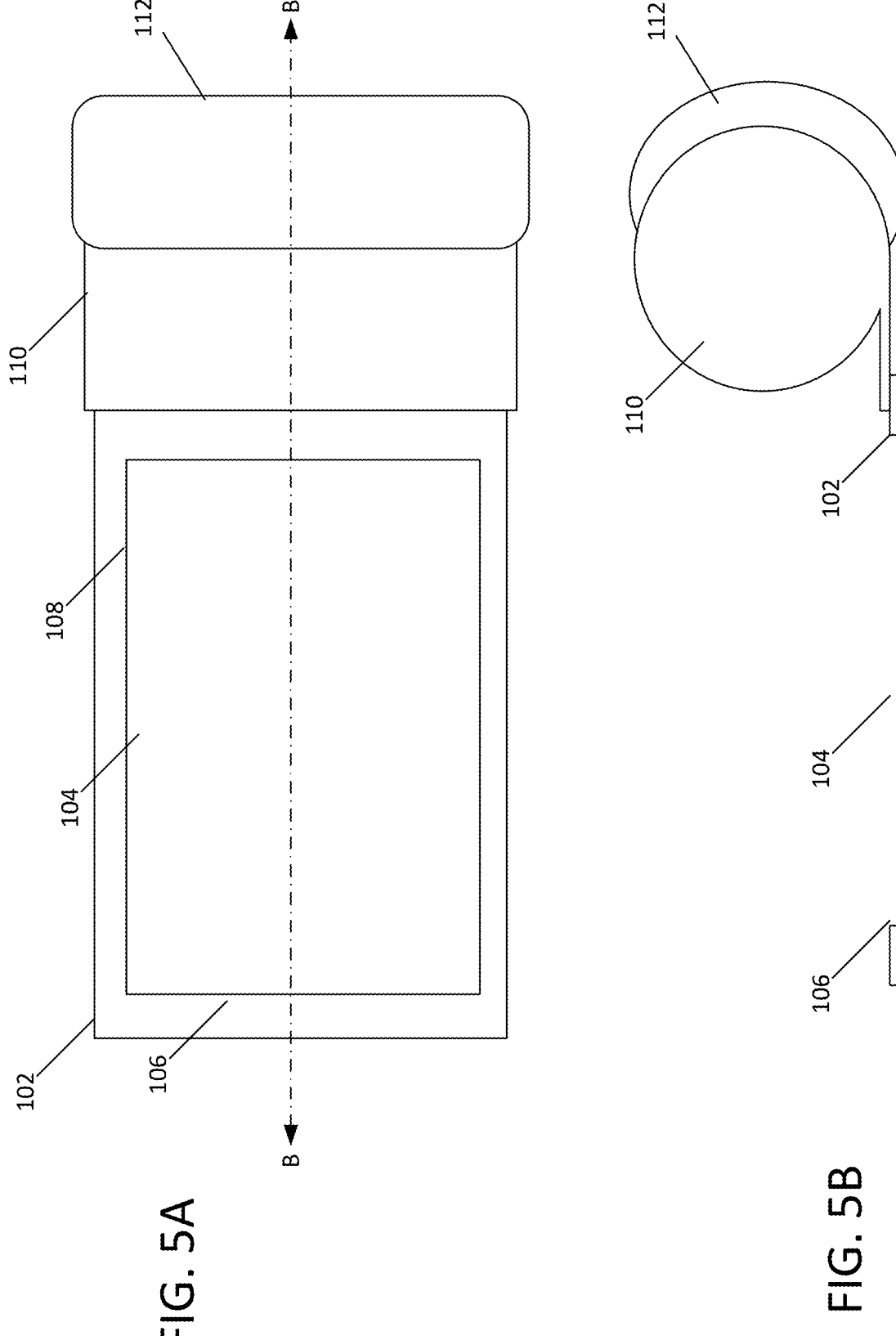
FIGS. 5A and 5B illustrate an embodiment of the enhanced trauma bandage in which the dressing 112 is offset from the reinforced pass-through region 102 with FIG. 5B being a cross-sectional view of FIG. 5A taken along line B-B''.
Figure 6B:
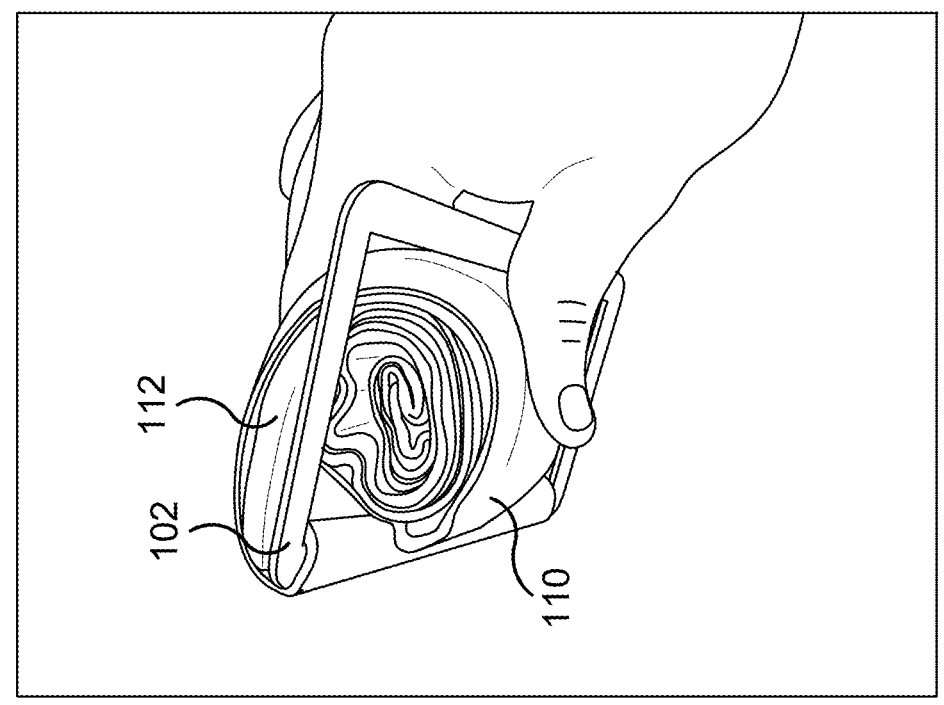
FIGS. 6A and 6B illustrate an embodiment of the enhanced trauma bandage according to FIG. 5A.
Figure 6A:
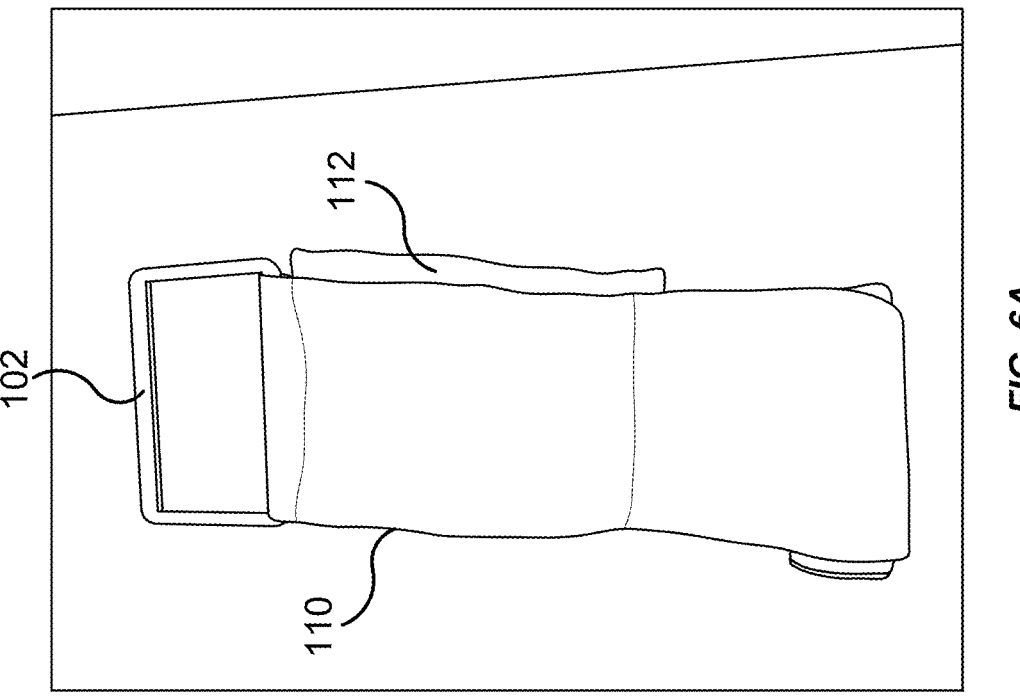

In most cases it is anticipated that a single ETB will be provided in a single pouch. In some embodiments, however, as illustrated in FIG. 3, a plurality of ETBs can be provided as a single unit that can be used in combination for covering larger areas and/or can be pulled apart or otherwise separated along lines 120 and used individually as illustrated in FIGS. 5A-B.

In some embodiments of the ETB, one or more regions may be provided on the exposed surface of the bandage 110 and/or the pass-through region 102 on which a medic or other personnel can record pertinent information such as the time of application, condition of the patient, medicines onboard, preliminary assessment of the injury, and/or other relevant data.

Other embodiments of the ETB may be provided with an attached tag (not shown), with or without a removable portion (not shown), for recording pertinent information for downstream health care workers for improving the visibility and transmission of the recorded information regardless of the manner and/or state of consciousness in which the injured party is delivered to a more advanced medical facility. These embodiments may increase the visibility of the recorded information regardless of the manner in which the ETB bandage is applied and save valuable diagnostic and/or treatment time downstream as the injured party is delivered to better equipped treatment facilities.

In some embodiments of the ETB, materials may be added or modifications made to the bandage so that the ETB is readily visible on images generated using various medical imaging techniques including, for example, X-rays, magnetic resonance imaging (MM) and computerized tomography (CT) scans. There are a number of different radiopaque polymeric materials and contrast agents that are currently used in combination with medical implants or inserts to enhance subsequent imaging, each with its own advantages and limitations. A conventional method for making medical devices and appliances more radiologically visible relies on blending polymers with conventional radiopaque agents, e.g., a physical mixture of one or more acrylic derivatives and inorganic salts and/or metal particles. Other methods can involve either the formation of one or more radiopaque polymer salt complexes entrapped in a crosslinked network and/or radiopaque polymers prepared from one or more monomers that incorporate a radiopaque element prior to polymerization.

In some embodiments, the concentration of the radiopaque element may be selected to render the ETB radio-translucent to allow for imaging of the body part(s) concealed under the ETB without the need to remove the ETB. In other embodiments, the distribution of the radiopaque element(s) within the ETB may be selected to render the boundaries of the ETB radiopaque while allowing a generally unobstructed imaging of the body part(s) under the ETB.

As will be appreciated by those skilled in the art, the basic ETB constructions and methods of use described herein may be modified in a variety of ways without departing from the concept as illustrated and described in the structures and functions detailed in the specification and illustrated in the associated Figures.

Such modifications are expected to include anchor points for securing the ETB to the body, attaching light sticks or other signaling devices, tensioning the bandage, and/or attaching a provided or improvised windlass for tourniquet applications. Other modifications are expected to include a MOLLE adapter (Modular Lightweight Load-carrying Equipment), multiple locations and configurations of the pass-through opening(s) or other structures used in securing or tensioning the ETB, modified compression wrap dispenser(s), modified bandage structure to allow use as a tourniquet, and/or point pressure pouches/areas and/or pressure point materials of various numbers, shapes, sizes, and designs for increasing the field treatment options.

A first embodiment includes a compression dressing having an elastic bandage roll; a pass-through structure attached to a first end of the elastic bandage roll, the pass-through structure including an opening and a bandage guide structure; a support surface provided on a lower surface of the pass-through structure; and an absorbent pad removably attached to the lower surface of the pass-through structure. A second embodiment of a compression dressing includes an elastic bandage roll; a pass-through structure attached to a first end of the elastic bandage roll, the pass-through structure including an opening and a bandage guide structure; and an absorbent pad removably attached to the lower surface of a first portion of the elastic bandage roll adjacent the pass-through structure. A third embodiment of a compression dressing includes an elastic bandage roll; a pass-through structure attached to a first end of the elastic bandage roll, the pass-through structure including an opening and a bandage guide structure; and one or more absorbent pad(s) configured for placement or attachment to the lower surface of a first portion of the elastic bandage roll adjacent the pass-through structure and/or a lower surface of the pass-through structure. Each of the embodiments of the compression dressing may be applied to, for example, a wounded limb, by positioning the absorbent pad over a damaged portion of the wounded limb; wrapping a first portion of the elastic bandage around the wounded limb in a first direction; passing a second portion of the elastic bandage through the pass-through region; tensioning the residual portion of the elastic bandage against the bandage guide structure; wrapping the second portion of the elastic bandage around the wounded limb in a second direction, the second direction being opposite the first direction; and securing a distal portion of the elastic bandage to maintain the compression dressing as illustrated in FIGS. 7A-7H.

The foregoing disclosure outlines features of several embodiments so that those skilled in the art may better understand the aspects of the present disclosure. Those skilled in the art should appreciate that they may readily use the present disclosure as a basis for designing or modifying other processes and structures for carrying out the same purposes and/or achieving the same advantages of the embodiments introduced herein. Those skilled in the art should also realize that such equivalent constructions do not depart from the spirit and scope of the present disclosure, and that they may make various changes, substitutions, and alterations herein without departing from the spirit and scope of the present disclosure.

I claim:

1. An enhanced trauma bandage, comprising:
   a) a bandage material in the form of a roll, bundle or folded stack;
   b) a pass-through region that is a ring, D-ring or eyelet, comprising a pass-through opening and a tensioning opening;
   c) a dressing support surface connecting the bandage material and the pass-through region, wherein the bandage material and the pass-through region are attached to an upper surface of the dressing support surface, and the bandage material is attached to the dressing support surface opposite the tensioning opening, wherein the pass-through region is removably attached to the upper surface of the dressing support surface; and
   d) a dressing removably attached to a lower surface of the dressing support surface;
   wherein the pass-through opening of the pass-through region is sized to allow the bandage material in its entirety in the form of the roll, bundle or folded stack to pass through and the tensioning opening is a linear opening.

2. The enhanced trauma bandage of claim 1, wherein the bandage material is configured to provide a degree of self-tack to allow the roll, bundle or folded stack to maintain its integrity until the enhanced trauma bandage is applied to a wound.

3. The enhanced trauma bandage of claim 1, wherein the bandage material is an elastic compression wrap.

4. The enhanced trauma bandage of claim 1, wherein the tensioning opening maintains substantially the full width of the bandage material during application to a wound.

5. The enhanced trauma bandage of claim 1, wherein the dressing support surface is formed from the bandage material.

6. The enhanced trauma bandage of claim 1, wherein the dressing is removably attached to the lower surface of the dressing support surface via adhesive, hook and loop fasteners, stitching, tack-stitching, needle-tacking or welding.

7. The enhanced trauma bandage of claim 1, wherein the pass-through region is removably attached to the upper surface of the dressing support surface by one or more attachments comprising rivets, adhesive, stitching, hook and loop fasteners, or welding.

8. The enhanced trauma bandage of claim 1, wherein the dressing comprises an absorbent material.

9. The enhanced trauma bandage of claim 8, wherein the absorbent material comprises foamed, woven, and/or non-woven material of natural and/or synthetic fibers selected from the group consisting of rayon, polyester, polyurethane, polyolefin, cellulose, cellulose derivatives, cotton, orlon, polymeric hydrogels, and mixtures and combinations thereof.

10. The enhanced trauma bandage of claim 8, wherein the absorbent material includes a coagulant and/or antibiotic/antimicrobial substance.

11. The enhanced trauma bandage of claim 8, wherein the absorbent material is configured to be expanded into a bag/pouch for covering and/or protecting a remaining stump of a body part after an amputation.

12. The enhanced trauma bandage of claim 1, further comprising a pocket on the pass-through region and/or the dressing support surface.

13. The enhanced trauma bandage of claim 1, wherein the dressing support surface is clear or translucent.

14. The enhanced trauma bandage of claim 1, further comprising a material to allow visibility of the enhanced trauma bandage using medical imaging techniques.

15. A method of applying the enhanced trauma bandage of claim 1 to a wound, comprising:
   a) placing the removably attached dressing on a surface of the wound;
   b) wrapping the bandage material in a first direction around a limb or body part on which the wound is located;
   c) passing the bandage material in its entirety in the form of the roll, bundle or folded stack through the pass-through opening of the pass-through region;
   d) pulling the bandage material against the tensioning opening to provide a desired level of compression over the wound;
   e) reversing the wrapping direction of the bandage material in a second direction, opposite the first direction, and over a previously applied portion of the bandage; and
   f) securing the bandage material to maintain the desired level of compression over the wound.

16. The method of claim 15, wherein a) through f) are carried out in a one-handed and/or self-application.

17. The method of claim 15, further comprising joining a second enhanced trauma bandage by passing a second bandage material in its entirety in the form of a roll, bundle or folded stack through the pass-through opening of the pass-through region to provide a longer bandage.

* * * * *